United States Patent [19]

Christidis et al.

[11] Patent Number: 4,515,970
[45] Date of Patent: May 7, 1985

[54] PROCESS FOR PREPARATION OF ALKANOIC ACIDS

[75] Inventors: Yani Christidis; Jean-Claude Vallejos, both of Paris, France

[73] Assignee: Societe Francaise Hoechst, Puteaux, France

[21] Appl. No.: 601,221

[22] Filed: Apr. 17, 1984

[30] Foreign Application Priority Data

Apr. 29, 1983 [FR] France ................. 83 07137

[51] Int. Cl.³ .............. C07D 333/24; C07C 63/36
[52] U.S. Cl. ............................. 549/79; 549/447; 562/490; 562/496
[58] Field of Search ............... 549/79, 447; 562/490, 562/496

[56] References Cited

PUBLICATIONS

Wagner & Zook, Synthetic Organic Chemistry, (1965), p. 432.

Primary Examiner—Alan Siegel
Attorney, Agent, or Firm—Karl W. Flocks; Sheridan Neimark

[57] ABSTRACT

A process for preparation of substituted acetic acids having the general formula I:

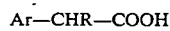

Ar—CHR—COOH        I in which R is selected from the group consisting in one hydrogen atom and $C_1$-$C_4$-alkyl radicals, and Ar is selected from the group consisting in radicals of aromatic nature selected from the following radicals: 2-thienyl, 2-methoxy-1-naphthyl, 3,4-methylenedioxyphenyl, and the substituted phenyls of the general formula II:

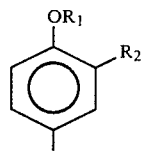

where $R_1$ is selected from the group consisting in hydrogen and $C_1$-$C_4$-alkyl groups, and $R_2$ is selected from the group consisting in hydrogen, halogen, alkyl, alkoxy and hydroxy-groups, such process comprising the step of reacting under heat in an acid medium, in the presence of red phosphorus and catalytic quantities of iodine or hydriodic acid, an alpha carbonylated carboxylic acid having the general formula III:

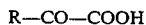

R—CO—COOH        III in which R has the same meaning as above with an unsaturated derivative of aromatic nature selected from the group consisting in thiophene, 2-methoxynaphthalene, 1,2-methylenedioxy-benzene, and the substituted aromatic hydrocarbons having the general formula IV:

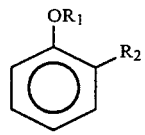

in which $R_1$, $R_2$ have the same meanings as above, possibly within a compatible organic solvent.

10 Claims, No Drawings

PROCESS FOR PREPARATION OF ALKANOIC ACIDS

This invention relates to a process for industrial manufacture of alkanoic acids, more particularly, it relates to a process for manufacture of substituted acetic acids designated hereinafter as arylacetic acids having the general formula I:

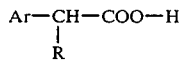

in which R represents a hydrogen atom or a $C_1$–$C_4$-alkyl radical and Ar represents a radical of aromatic nature selected among the following radicals: 2-thienyl, 2-methoxy-1-naphthyl, 3,4-methylenedioxy-phenyl, and the substituted phenyls having the general formula II:

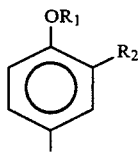

where $R_1$ represents a hydrogen atom or a $C_1$–$C_4$-alkyl group and $R_2$ represents a hydrogen atom, a halogen atom, an alkyl, alkoxy or hydroxy group. The aryl acetic acids having the general formula I are widely described in the literature. They are in particular raw materials interesting for synthesis of active pharmaceutical substances.

Therefore it is of great interest of being able to prepare them as rationally as possible.

Very numerous methods are known for preparation of substituted acetic acids. Among them, the WILLGERODT-KINDLER's reaction which authorizes transformation of an arylalkylketone to arylalkylcarboxylic acid is one of the most known reactions. However, generally it only provides from moderate to poor yields and leads to secondary sulfureous products responsible for a pollution which today is found unacceptable. To remedy such inconveniences more elaborate methods have been developed requiring the use of several reactional steps such as in particular hydrogenolysis either chemical or catalytic, of arylglycolic acids, arylglycolic o-acylated acids or 2-aryl-2-halogeno alkanoic acids resulting in certains cases from condensation of glyaxylic acid over the corresponding aromatic derivative (European patent applications No. 0.032.374 and 0.028.375, European Pat. No. 0.003.825), the hydrolysis of an arylalkylacetonitrile obtained by reaction of the cyanide ion over a quaternized suitably substituted benzylamine (European patent application No. 0.062.440). Such methods, certain being very recent, require as the starting raw material products which are rarely available on the market, thereby necessitating their preliminary preparation with the disadvantages implied thereby.

However, the Applicant has discovered surprisingly that it was possible to obtain arylacetic acids having the general formula I in one step by hot reaction in acid medium in the presence of red phophorus and catalytic quantities of iodine or hydroiodic acid, of an alpha carbonylated carboxylic acid having the general formula III, R—CO—COOH, in which R has the meaning given above, with an unsaturated derivative of aromatic nature selected among the following: thiophene, 2-methoxy-naphthalene, 1,2-methylenedioxy-benzene or 1,3-benzodioxole, and the substituted aromatic hydrocarbons having the general formula IV, in which $R_1$ and $R_2$ have the meanings as given above:

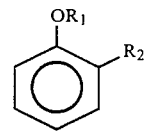

This class of unsaturated products of aromatic nature will be designated hereinafter by A.

Although correlatively to the formation of one mole of arylacetic acid having the general formula I, one mole of water is formed, it is sometimes advantageous to carry out the processs of this invention in the presence of small supplementary quantities of water.

More particularly, the process according to this invention comprises of reacting, at a temperature of between 30° and 100° C. in an acid medium, one mole of an alpha carbonylated carboxylic acid having the general formula III with from 1 to 10 moles of a derivative belonging to the class A, in the presence of 0.5 to 5 atom-grams of red phosphorus, from 0.5 to 2 moles of water and from 0.01 to 0.1 mole of iodine or hydriodic acid, possibly within a compatible organic solvent such as acetic acid, then isolating the desired acid having the general formula I by means known in themselves.

Advantageously, the process according to this invention comprises of reacting at a temperature of between 50° and 80° C. in acid medium one mole of glyoxylic acid or pyruvic acid with from 1 to 10 moles of a derivative belonging to the class A in the presence of 0,5 to 3 atomgrams of red phosphorus, from 0.5 to 2 moles of water and from 0.025 to 0.05 mole of iodine or hydriodic acid possibly within acetic acid, then isolating the desired acid having the formula I by means known in themselves.

The hydriodic acid is the commercial hydriodic acid in aqueous solution at 57% by weight.

According to a modified form of embodiment, the process of this invention can be carried out in the presence of 0.001 to 1 mole, advantageously from 0.005 to 0.3 mole of an organic sulfonic acid such as methanesulfonic acid per one mole of alpha carbonylated carboxylic acid having the general formula III engaged therein. The reactional duration of the process of this invention depends on the utilized substrates; usually such duration is of between 4 and 20 hours.

Preferably, the alpha carbonylated carboxylic acid having the general formula III is glyoxylic acid or pyruvic acid. The glyoxylic acid used is generally glyoxylic acid in aqueous solution at 80% by weight.

Upon completion of the reaction, the desired arylacetic acid having the general formula I is isolated from the reactional medium by means known in themselves. Generally, phosphorus not transformed by filtration is eliminated from the reactional medium returned to the ambient temperature, then the filtrate is treated with sodium acetate to neutralize any hydroiodic acid and/or organic sulfonic acid present.

The filtrate is then concentrated under vacuum at a controlled temperature to eliminate only the reactional solvent and/or the starting product which has not reacted. The so obtained concentrate is dissolved in a compatible, water-immiscible, organic solvent and the obtained solution is washed first with water containing sodium metabisulfite in solution, then with water, finally it is concentrated dry under vacuum. Thus, there is isolated the desired arylacetic acid having the general formula I which can as necessary be purified by recrystallization.

With certain substrates it is sometimes advantageous to isolate the desired arylacetic acid in form of sodic salt, then move such salt by concentrated hydrochloric acid.

The process of this invention permmits to obtain among others the following acids:
2-thiophene acetic acid;
paramethoxyphenylacetic acid;
3,4-dimethoxyphenylacetic acid;
3-chloro-4-hydroxy-phenylacetic acid;
3,4-methylenedioxy-phenylacetic acid;
(2-methoxy-1-naphthalene)-acetic acid;
2-methyl-2-parahydroxyphenyl acetic acid;
thiophene-2-methyl acetic acid.

All such acids are precious raw materials for preparation of therapeutical activity substances.

The following Examples are given by way of explanation and do not at all limit the invention.

EXAMPLE 1

There is heated for 6 hours at 50° C. under stirring a suspension of:
46.3 g (0.5 mole) of glyoxylic acid at 80% by weight in water;
210 g (2.5 moles) of thiophene;
1.65 cm3 (0.0125 mole) of hydriodic acid at 57%, d=1.7;
0.25 g (0.0025 mole) of methanesulfonic acid at 98%;
23.3 g (0.75 at.g.) of red phosphorus;
250 cm3 of pure crystallizable acetic acid.

Then the reactional medium cooled to the ambient temperature is filtered to eliminate the unreacted phosphorus. The filtrate treated by 1.23 g (0.015 mole) of pure dry sodium acetate is then concentrated under vacuum of 20 mm Hg up to reaching a temperature of 60° C. After cooling to the ambient temperature 125 cm3 of dichloroethane is introduced into this concentrated medium, it is decanted, then the organic phase is washed with a solution of 80 g of water containing 15 g of sodium chloride and 3 g of sodium metabisulfite. The organic phase if then concentrated dry under vacuum and the oily residue (36.5 g) is distilled under vacuum (0.6 mm Hg). Thus, 35.5 g (0.25 mole) of 2-thiophene acetic acid is collected distilling at 94° C. and presenting a melting point of 62±1° C. The yield is determined to 50% of the theoretical value calculated with respect to the glyoxylic acid used.

EXAMPLE 2

There is heated for 390 minutes at 70° C. under stirring a suspension of:
277.5 g (3 moles) of glyoxylic acid at 80% by weight in water;
972 g (9 moles) of anisole;
21 g (0.0827 mole) of pure bisublimed iodine;
279 g (9 at.g.) of red phosphorus;
600 cm3 of pure crystallizable acetic acid.

Then, the reactional medium cooled to the ambient temperature is filtered to eliminate the unreacted phosphorus. The filtrate treated by 14 g (0.17 mole) of dry pure sodium acetate is then concentrated under vacuum of 20 mm Hg. The residue is taken up again with 400 cm3 of water and 600 cm3 of ethylic ether. It is decanted and the ethereal phase is washed off first with an aqueous solution at 5% by weight of sodium metabisulfite and then water. The organic phase is then concentrated dry under vacuum and the oily residue (455 g) is distilled under vacuum. Thus, there is collected 368.8 g (2.22 moles) of paramethoxyphenyl acetic acid distilling at 180±3° C. under a 3mm Hg-vacuum and having a melting point of 85±1° C. The yield is determined to 74% of the theoretical value as calculated with respect to the glyoxylic acid used.

EXAMPLE 3

There is heated for 16 hours at 70° C. under stirring a suspension of:
46.3 g (0.5 mole) of glyoxylic acid at 80% by weight in water;
183 g (1.5 moles) of 1,2-methylenedioxy-benzene;
46.5 g (1.5 at.g.) of red phosphorus;
3.3 cm3 (0.025 mole) of hydriodic acid at 57%, d=1,7;
10 g (0.102 mole) of methanesulfonic acid at 98%;
250 cm3 of acetic acid.

Thereafter, the reactional medium cooled to the ambient temperature is filtered to eliminate the unreacted phosphorus. The filtrate treated by 10.5 g (0.128 mole) of pure dry sodium acetate is then concentrated dry under vacuum. The oily residue is taken up again with a mixture of water and sulfuric ether. It is decanted and the ethereal phase is washed with an aqueous solution of sodium bisulfite, then water.

Through dry concentration under vacuum of the organic phase, there is collected 84.5 g of partly crystallized product which crystallizes by heat and cold in 6 volumes of a ¼ v/v acid acetic and water mixture. There is thus isolated 53.6 g(0.2976 mole) of crystallized 3,4-methylenedioxyphenyl acetic acid having a melting point of 127±1° C. The yield is determined to 59.5% of the theory as calculated with respect to the glyoxylic acid used.

EXAMPLE 4

There is heated for 4 hours at 80° C. under stirring a suspension of:
46.3 g (0.5 mole) of glyoxylic acid at 80% by weight in water;
80.35 g (0.625 mole) of orthochlorophenol;
1.65 cm3 (0.0125 mole) of hydriodic acid at 57%, d=1.7;
5 g (0.05 mole) of methanesulfonic acid at 98%;
19 g (0.6 at.g.) of red phosphorus;

Thereafter, the reactional medium is poored into 100g of icy water; the obtained suspension is filtered and the filtrate is treated with 30 cm3 of 30% NaOH (0.3 mole) and then it is submitted to water steam carrying step to eliminate the unreacted orthochlorophenol. Thus, there is recovered 32 g of orthochlorophenol i.e. 0.25 mole. The water steam carrying step residue is brought to pH=7, with 30% NaOH. The sodium salt of 3-chloro-4-hydroxyphenyl acetic acid crystallizes. It is squeezed, then dried under vacuum at 110° C. at constant weight. Thus, there is isolated 66 g of crystallized sodium 3-chloro-4-hydroxy phenylacetate. Such salt is brought into suspension in a volume of water at 50° C.; then, concentrated hydrochloric acid is introduced up to obtaining a pH=1. An oil is formed which crystallizes slowly. The crystallized product is squeezed, then dried under vacuum at 70° C. at constant weight. There is collected 53.5 g (0.286 mole) of 3-chloro-4-hydroxyphenyl acetic acid, crystallized and having a melting point of 108±1° C. The yield is determined to 57.3% of the theory as calculated in respect to the glyoxylic acid used.

EXAMPLE 5

There is heated under stirring for 16 hours at 70° C. a suspension of:

46.3 g (0.5 mole) of 80%-glyoxylic acid in water;
69 g (0.5 mole) of veratrole;
3.3 cm3 (0.025 mole) of hydriodic acid at 57%, d=1.7;
10 g (0.1 mole) of methanesulfonic acid at 98%;
46.5 g (1.5 at.g.) of red phosphorus;
250 cm3 of acetic acid.

Then the reactional medium is treated as described in Example 2. Thus, there is collected 68.7 g of raw 3,4-dimethoxyphenyl acetic acid which is purified by dissolution in 525 cm3 of water containing 17.5 g of sodium hydroxide, the resulting aqueous solution is washed with sulfuric ether, then the desired acid is precipitated by adding concentrated hydrochloric acid up to pH=1. There is thus isolated 48.1 g (0.245 mole) of crystallized 3,4-dimethoxyphenyl acetic acid having a melting point of 97±1° C. The yield is determined to 49% of the theory as calculated in respect to the glyoxylic acid used.

EXAMPLE 6

There is heated for 8 hours at 75° C. under stirring a suspension of:

46.3 g (0.5 mole) of glyoxylic acid at 80% by weight in water;
237.5 g (1.5 moles) of 2-methoxy-naphthalene;
5 g (0.02 mole) of pure bisublimed iodine;
46.5 g (1.5 at.g.) of red phosphorus;
175 cm3 of pure crystallizable acetic acid.

Then the reactional medium is cooled to the ambient temperature. It sets to a mass. It is taken up again by 650 cm3 of ethyl acetate in reflux, it is filtered hot and the filtrate is concentrated dry under vacuum. The residue is taken up again by sulfuric ether and by an aqueous solution saturated with sodium bicarbonate. It is decanted and the aqueous phase is acidified to pH=1 with concentrated hydrochloric acid. The desired product crystallizes. It is squeezed, then dried under vacuum at 100° C. at constant weight. Thus, there is isolated 20 g (0.0925 mole) of crystallized 2-methoxy-naphthalene acetic acid having a melting point of 216±1° C. The yield is determined to 18.5% of the theory as calculated in respect to the glyoxylic acid used.

EXAMPLE 7

There is heated for 10 hours at 75° C. under stirring a suspension of:

44 g (0.5 mole) of pyruvic acid;
420 g (5 moles) of thiophene;
3.3 cm3 (0.025 mole) of hydriodic acid at 57%, d=1.7;
13 g (0.13 mole) of methanesulfonic acid at 98%;
46.5 g (1.5 at.g.) of red phosphorus;
200 cm3 of pure crystallizable acetic acid;
10 g of water.

Then, the reactional medium cooled to the ambient temperature is filtered. The filtrate treated by 13.2 g (0.161 mole) of pure dry sodium acetate is then concentrated dry under vacuum.

The oily residue is taken up again with sulfuric ether, then such solution is washed with water containing in solution 3% by weight of sodium metabisulfite, and it is then concentrated dry under vacuum. There is thus obtained 65 g of oil which is distilled under vacuum. 48.9 g of 2-methyl-2-(2-thienyl)acetic acid distilling under vacuum of 8 mm Hg at 144±2° C. The yield is determined to 62.6% of the theoretical value as calculated in respect to the pyruvic acid used.

EXAMPLE 8

There is heated for 7 hours at 75° C. under stirring a suspension of:

44 g (0.5 mole) of pyruvic acid;
70.5 g (0.75 mole) of phenol;
3.3 cm3 (0.025 mole) of 57%-hydriodic acid, d=1.7;
4.9 g (0.05 mole) of methanesulfonic acid at 98%;
23 (0.74 at.g.) of red phosphorus;
50 cm3 of pure crystallizable acetic acid;
10 g of water.

Then, the reactional medium cooled to the ambient temperature is filtered. The filtrate treated with 6.5 g (0.08 mole) of pure dry sodium acetate is then concentrated dry. The residue is taken up with 400 g of water and sufficient quantity of NaOH at 20% by weight to obtain a solution of a pH=6. Such solution is washed with ethylic ether, then acidified to pH=1.5, with concentrated hydrochloric acid.

The desired acid is then extracted with ethylic ether, then isolated in the raw condition by vacuum elimination of the extraction solvent.

Thus, there is isolated 40 g of raw crystallized acid which is purified by distillation under vacuum ($E_{0.1}=150\pm4°$ C.). The distillate crystallizes on cooling. There is thus obtained 2-parahydroxyphenyl-2-methyl acetic acid having a melting point of 130±2° C.

It will be understood that this invention was only described in a purely explanative and not at all limitative manner and that any useful modification can be effected therein without however departing from its scope as defined in the appended claims.

We claim:

1. A process for preparation of substituted acetic acids having the general formula I:

Ar—CHR—COOH         I in which R is selected from the group consisting of one hydrogen atom and $C_1$–$C_4$-alkyl radicals, and Ar is selected from the group consisting of radicals of aromatic nature selected from the following radicals: 2-thienyl, 2-methoxy-1-naphthyl, 3,4-methylenedioxyphenyl, and the substituted phenyls of the general formula II:

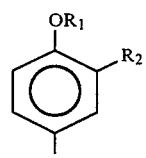

where $R_1$ is selected from the group consisting of hydrogen and $C_1$–$C_4$-alkyl groups, and $R_2$ is selected from the group consisting of hydrogen, halogen, alkyl, alkoxy and hydroxy-groups, such process comprising the step of reacting under heat in an acid medium, in the presence of red phosphorus and catalytic quantities of iodine or hydriodic acid, an alpha carbonylated carboxylic acid having the general formula III:

R—CO—COOH   III in which R has the same meaning as above with an unsaturated derivative of aromatic nature selected from the group consisting in thiophene, 2-methoxynaphthalene, 1,2-methylenedioxy-benzene, and the substituted aromatic hydrocarbons having the general formula IV:

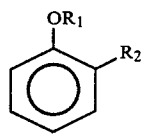   IV in which $R_1$, $R_2$ have the same meanings as above.

2. A process as in claim 1, comprising reacting at a temperature of between 30° and 100° C. in an acid medium one mole of alpha carbonylated carboxylic acid having the general formula III such as defined in said claim 1, with from 1 to 10 moles of an unsaturated derivative of an aromatic nature such as defined in claim 1 in the presence of 0.5 to 2 moles of water and from 0.01 to 0.1 mole of iodine or hydriodic acid.

3. A process as in claim 1, comprising reacting at a temperature of between 50° and 80° C. in an acid medium 1 mole of an acid selected from the group consisting in glyoxylic acid and pyruvic acid, with from 1 to 10 moles of an unsaturated derivative of an aromatic nature such as defined in said claim 1, in the presence of 0.5 to 3 atom-grams of red phosphorus, from 0.5 to 2 moles of water and from 0.025 to 0.05 mole of iodine or hydriodic acid.

4. A process as in claim 1, which is carried out in the presence of 0.001 to 1 mole of an organic sulfonic acid per one mole of alpha carboxylated carboxylic acid used.

5. A process as in claim 4, wherein the organic sulfonic acid used is methanesulfonic acid.

6. A process as in claim 1, wherein the unsaturated derivative of aromatic nature used is thiophene, and the alpha carbonylated carboxylic acid used is glyoxylic acid, whereby 2-thiophene acetic acid is obtained.

7. A process as in claim 1, wherein the unsaturated derivative of aromatic nature used is thiophene, and the alpha carbonylated carboxylic acid used is pyruvic acid, whereby 2-thiophene-2-methyl acetic acid is obtained.

8. A process as in claim 1, wherein the unsaturated derivative of aromatic nature used is anisole and the alpha carbonylated carboxylic acid used is glyoxylic acid whereby paramethoxyphenyl acetic acid is obtained.

9. A process as in claim 1, wherein the unsaturated derivative of aromatic nature used is orthochlorophenol and the alpha carbonylated carboxylic acid used is glyoxylic acid whereby 3-chloro-4-hydroxyphenyl acetic acid is obtained.

10. A process as in claim 1, wherein the unsaturated derivative of aromatic nature used is phenol and the alpha carbonylated carboxylic acid used is pyruvic acid whereby 2-methyl-parahydroxyphenyl acetic acid is obtained.

* * * * *